United States Patent
Morita et al.

(10) Patent No.: US 6,641,805 B1
(45) Date of Patent: Nov. 4, 2003

(54) COPOLYMER FOR COSMETIC PREPARATION

(75) Inventors: Masamichi Morita, Settsu (JP); Motonobu Kubo, Settsu (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 09/646,784

(22) PCT Filed: Mar. 17, 1999

(86) PCT No.: PCT/JP99/01304

§ 371 (c)(1),
(2), (4) Date: Nov. 1, 2000

(87) PCT Pub. No.: WO99/48464

PCT Pub. Date: Sep. 30, 1999

(30) Foreign Application Priority Data

Mar. 23, 1998 (JP) .......................................... 10/074234

(51) Int. Cl.[7] ................................................ A61K 7/48
(52) U.S. Cl. ...................... 424/78.03; 424/69; 424/401; 514/63; 526/243; 526/245; 528/26
(58) Field of Search ....................... 424/401, 69, 78.03; 514/63; 526/243, 245; 528/26

(56) References Cited

U.S. PATENT DOCUMENTS 5,840,291 A    11/1998  Tsubakihara et al.
5,945,108 A  *  8/1999  Sugawara et al. .......... 424/401
6,136,331 A  * 10/2000  Morita et al. ................ 424/401

FOREIGN PATENT DOCUMENTS

| EP | A10766957 | 4/1997 |
| JP | A2247110 | 10/1990 |
| JP | B2346444 | 7/1991 |
| JP | A912428 | 1/1997 |
| JP | A9110633 | 4/1997 |
| JP | A9157339 | 6/1997 |

* cited by examiner

Primary Examiner—Jyothsan Venkat
(74) Attorney, Agent, or Firm—Birch, Stewart, Kolasch & Birch, LLP

(57) ABSTRACT

The polymer for cosmetics produced by polymerizing (A) a fluorine-containing (meth)acrylate, and (B) at least one silicon-containing polymerizable compound selected from the group consisting of a mercapto-modified silicone, an azo group-containing silicone and a polymerizable silane can be blended easily in cosmetic preparations and can form a film excellent in a water proofing property, a water- and oil-repellency, feelings in use and safety. This copolymer for cosmetics can improve the drawbacks of fluorine compound-treated powders.

20 Claims, No Drawings

COPOLYMER FOR COSMETIC PREPARATION

FIELD OF THE INVENTION

The present invention relates to a copolymer for cosmetics which can be blended easily in a cosmetics preparation and is excellent in a waterproofing property, a water- and oil-repellency, feelings in use and safety, and to cosmetics characterized by containing the copolymer. The copolymer functions as a film-forming agent for cosmetics, a compatibilizer and emulsifier for a fluorine-containing raw material and a fluorine-free raw material, and a surface-treatment agent for fluorine compound-treated powders and silicone-treated powders.

RELATED ART

Heretofore, hydrocarbon-based emulsion resins have been used as film-forming agents for cosmetics. These are blended for the purpose of holding pigments or effective components in preparations on the skin for a long period of time by forming films after their application. However, because of their insufficient waterproofing properties and water- and oil-repellency, they are disadvantageous in that the films are broken by the contact with water or by sweat or sebum excreted from the skin. In addition, an acryl-silicone copolymer which has improved the drawbacks in the waterproofing property and the water-repellency of the hydrocarbon-based emulsion resins is in use recently (Japanese Patent Kokai Publication No. 2-247110 (247110/1990)). This is a copolymer of hydrocarbon-based acrylate and a silicone macromonomer, a film thereof being excellent in the waterproofing property and the water-repellency.

However, since the acryl-silicone copolymer also has low oil-repellency, it can not prevent the coming off of make-up caused by sebum. On the other hand, there is known a technique which contains a copolymer of an alkyl (meth)acrylate having a long-chain alkyl group having 8 or more carbon atoms and a polyfluoroalkyl (meth)acrylate having a polyfluoroalkyl group having 4 or more carbon atoms as a film-forming component in order to imparting the oil-repellency (Japanese Patent Kokoku Publication No. 3-46444 (46444/1991)). However, since this copolymer has a higher softening temperature than the skin temperature, it does not form any film in the form of emulsion dispersing in water. A copolymer having such a reduced molecular weight that the copolymer can dissolve in a solvent in order to form a film has no oil-repellency.

On the other hand, fluorine-containing raw materials such as a fluorine compound-treated powder and perfluoropolyether have recently come to be blended in cosmetic preparations. Since these fluorine-containing raw materials have poor affinities with fluorine-free raw materials such as those of hydrocarbon type and of silicone type which have been used widely, it is very difficult to blend them in preparations with stability. Therefore, the development of compatibilizers for the improvement in affinities between fluorine-containing raw materials and fluorine-free raw materials has been demanded.

SUMMARY OF THE INVENTION

According to the present invention, an intensive study for solving the above problems has made clear that when a fluorine-containing (meth)acrylate copolymer having a specific composition is dissolved or dispersed in water or solvents, the copolymer exhibits excellent properties as a copolymer for cosmetics. The copolymer for cosmetics of the present invention can be blended easily in conventional cosmetic preparations, and the cosmetics in which the copolymer is blended can form films excellent in waterproofing properties, water- and oil-repellency, feelings in use and safety after their application on the skin.

Furthermore, this copolymer for cosmetics serves as a compatibilizer between fluorine-containing raw materials and fluorine-free raw materials, whereby having the effect of stabilizing cosmetic preparations.

The present invention provides a copolymer for cosmetics comprising (A) 5 to 99 parts by weight of repeating units derived from a fluorine-containing (meth)acrylate, and (B) 95 to 1 parts by weight of repeating units derived from at least one silicon-containing polymerizable compound selected from the group consisting of a mercapto-modified silicone, an azo group-containing silicone and a polymerizable silane.

DETAILED DESCRIPTION OF THE INVENTION

The copolymer of the present invention may comprise (C) 1 to 50 parts by weight of repeating units derived from at least one fluorine-free monomer selected from the group consisting of a polylakyleneglycol (meth)acrylate, an alkyl (meth)acrylate macromonomer and an alkyl (meth)acrylate, in addition to the repeating units (A) and (B).

The copolymer may be:

(i) a copolymer comprising the fluorine-containing (meth)acrylate and the mercapto-modified silicone;

(ii) a copolymer comprising the fluorine-containing (meth)acrylate and the azo group-containing silicone;

(iii) a copolymer comprising the fluorine-containing (meth) acrylate and the polymerizable silane;

(iv) a copolymer comprising the fluorine-containing (meth) acrylate, at least one silicon-containing polymerizable compound selected from the group consisting of mercapto-modified silicone, azo group-containing silicone and polymerizable silane, and the polyalkyleneglycol (meth)acrylate;

(v) a copolymer comprising the fluorine-containing (meth)acrylate, at least one silicon-containing polymerizable compound selected from the group consisting of the mercapto-modified silicone, the azo group-containing silicone and the polymerizable silane, and the alkyl (meth)acrylate macromonomer; or (vi) a copolymer comprising the fluorine-containing (meth)acrylate, at least one silicon-containing polymerizable compound selected from the group consisting of the mercapto-modified silicone, the azo group-containing silicone and the polymerizable silane, and the alkyl (meth)acrylate.

The fluorine-containing (meth)acrylate used for the copolymer for cosmetics has, for example, the following structural formula (I-1):

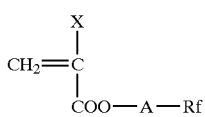

(I-1)

wherein Rf is a polyfluoroalkyl or perfluoropolyether group having 6 to 16 carbon atoms, A is an alkylene group having 1 to 4 carbon atoms or

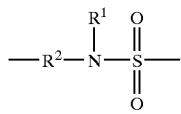

wherein $R^1$ is an alkyl group having 1 to 4 carbon atoms and $R^2$ is an alkylene group having 1 to 4 carbon atoms, or

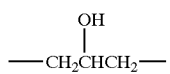

and X is a hydrogen atom or a methyl group.

The fluorine-containing (meth)acrylate may be, for example, a fluorine-containing (meth)acrylate macromonomer having the following structural formula (I-2):

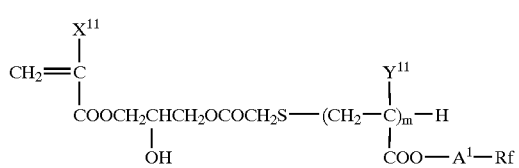

(I-2)

wherein Rf is a polyfluoroalkyl or perfluoropolyether group having 6 to 16 carbon atoms, $A^1$ is an alkylene group having 1 to 4 carbon atoms or

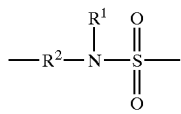

wherein $R^1$ is an alkyl group having 1 to 4 carbon atoms and $R^2$ is an alkylene group having 1 to 4 carbon atoms, or

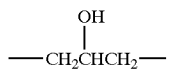

and $X^{11}$ is a hydrogen atom or a methyl group, $Y^{11}$ is a hydrogen atom or a methyl group and m is from 5 to 100.

The polyfluoroalkyl group (Rf group) may be a perfluoroalkyl group.

The perfluoropolyether group is specifically as follows:

$F(CF(CF_3)CF_2O)_nCF_2CF_2-$ wherein n is an integer of from 3 to 30, $CF_3O(CF(CF_3)CF_2O)_n(CF_2O)_mCF_2-$ wherein n is an integer of from 2 to 30 and m is an integer of from 3 to 70, $CF_3O(CF_2CF_2O)_n(CF_2O)_mCF_2-$ wherein n is an integer of from 2 to 40 and m is an integer of from 4 to 70, and $F(CF_2CF_2CF_2O)_nCF_2CF_2-$ wherein n is an integer of from 3 to 30.

The number average molecular weight (determined by $^{19}$F-NMR) of the perfluoropolyether group is preferably in the range of from 500 to 5,000.

Examples of the fluorine-containing (meth)acrylate are as follows:

$CF_3(CF_2)_7(CH_2)OCOCH=CH_2$,
$CF_3(CF_2)_6(CH_2)OCOC(CH_3)=CH_2$,
$(CF_3)_2CF(CF_2)_6(CH_2)_2OCOCH=CH_2$,
$CF_3(CF_2)_7(CH_2)_2OCOC(CH_3)=CH_2$,
$CF_3(CF_2)_7(CH_2)_2OCOCH=CH_2$,
$HCF_2(CF_2)_7(CH_2)_2OCOCH=CH_2$,
$CF_3(CF_2)_5(CH_2)_2OCOCH=CH_2$,
$CF_3(CF_2)_7SO_2N(CH_3)(CH_2)_2OCOCH=CH_2$,
$CF_3(CF_2)_7SO_2N(C_2H_5)(CH_2)_2OCOC(CH_3)=CH_2$,
$(CF_3)_2CF(CF_2)_6CH_2CH(OCOCH_3)CH_{2OCOC(CH3)}=CH_2$,
$(CF_3)_2CF(CF_2)_6CH_2CH(OH)CH_2OCOCH=CH_2$,

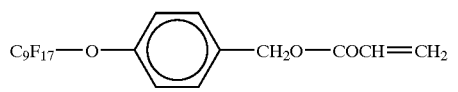

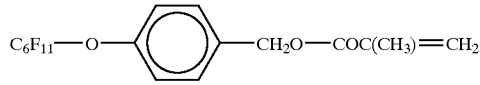

$F(CF(CF_3)CF_2O)_{10}CF_2CF_2-COOCH_2CH_2CH=CH_2$,

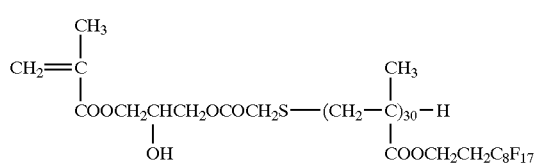

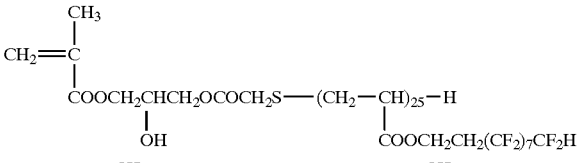

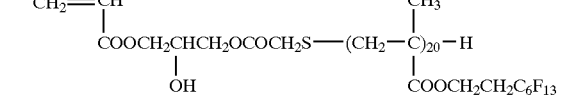

These fluorine-containing (meth)acrylates may be used in admixtures of at least two of them.

In the present invention, the silicon-containing polymerizable compound which undergoes radical polymerization with the fluorine-containing (meth)acrylate is the mercapto-modified silicone, the azo group-containing silicone or the polymerizable silane.

The mercapto-modified silicone is a silicone having at least one SH group. The mercapto-modified silicone has, for example, the following general formula (II-1-1) or (II-1-2).

General formulas (II-1-1) and (II-1-2):

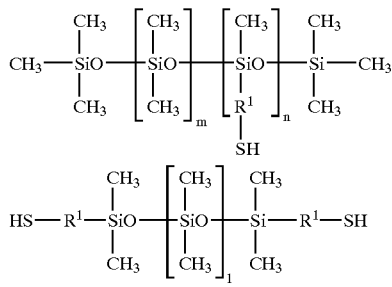

In the formulas, $R^1$ is a divalent saturated hydrocarbon group having a linear or branched carbon chain which may be intervened by one or two ether linkages, l is from 10 to 20, m is from 10 to 200 and n is from 1 to 10.

Specific examples of the mercapto-modified silicone are as follows:

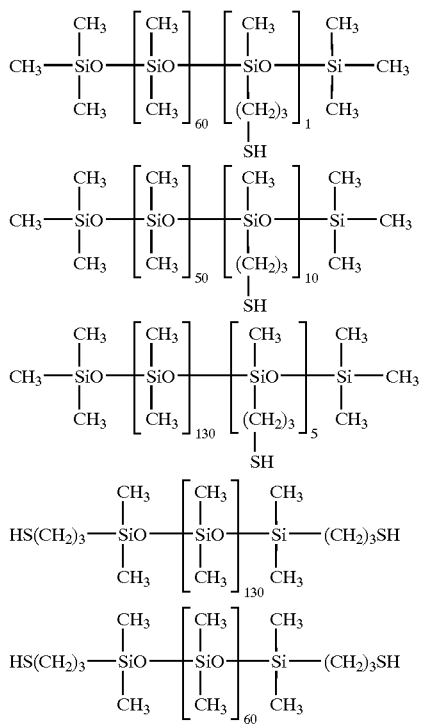

The azo group-containing silicone may be a silicone having an azo group and a urethane linkage. The azo group-containing silicone has, for example, the following general formula (II-2).

General formula (II-2):

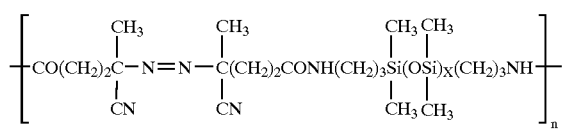

In the formula, x is from 10 to 200 and n is from 1 to 20.

Specific examples of the azo group-containing silicone are as follows:

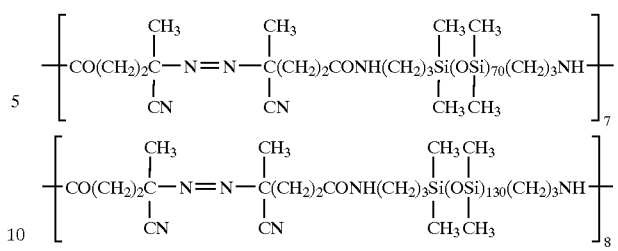

The polymerizable silane is a compound having an ethylenically unsaturated double bond and a siloxane bond. The polymerizable silane has, for example, the following general formula (II-3-1) or (II-3-2):

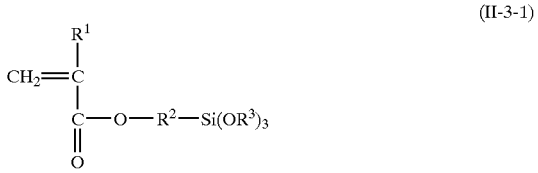

or $$CH_2=CHSi(OR^3)_3 \quad (II\text{-}3\text{-}2)$$

wherein $R^1$ is a methyl group or a hydrogen atom, $R^2$ is a divalent saturated hydrocarbon group having a linear or branched carbon chain which may be intervened by one or two ether linkages, and $R^3$ is an alkyl group having 1 to 4 carbon atoms.

Specific examples of the polymerizable silane are as follows.

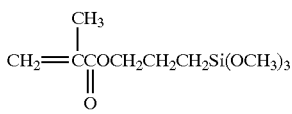

These silicon-containing polymerizable compounds may be used in admixtures of at least two of them.

In the present invention, when the mercapto-modified silicone or the azo group-containing silicone is used, the silicone component bonds to the end of the fluorine-containing (meth)acrylate copolymer to give a block or graft copolymer. Known general methods for synthesizing block or graft copolymers include (1) a chain transfer method, (2) a polymer initiator method, (3) a mechanical chemical reaction method, (4) a bonding (addition, condensation) reaction method, (5) an exchange reaction method, (6) a living polymer method, (7) a group transfer polymerization method, (8) a iodine transfer polymerization method and the like. The mercapto-modified silicone of the present invention gives block or graft copolymers by (1) the chain transfer method, and the azo group-containing silicone of the present invention gives block or graft copolymers by (2) the polymer initiator method.

Although the block or graft copolymers can be produced even if any of the methods (1) to (8) is used, the methods other than the methods (1) and (2) have problems of having complicated operations or achieving low yields. In the present invention, (1) the chain transfer method and (2) the polymer initiator method are preferably used, because they have features of being easy to produce the polymers industrially and of achieving high yields.

The polymer of the present invention may have (C) repeating units derived from at least one fluorine-free monomer selected from the group consisting of a polyalkyleneglycol (meth)acrylate, an alkyl (meth)acrylate macromonomer and an alkyl (meth)acrylate.

The polyalkyleneglycol (meth)acrylate has, for example, the following structural formula (III-1):

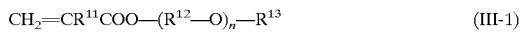

(III-1)

wherein $R^{11}$ and $R^{13}$ are a hydrogen atom or a methyl group, $R^{12}$ is an alkylene group having 2 to 6 carbon atoms and n is an integer of from 1 to 50.

Specific examples thereof include 2-hydroxyethyl (meth) acrylate and

wherein n is 2, 5 or 8.

The alkyl (meth)acrylate macromonomer has, for example, the following structural formula (III-2):

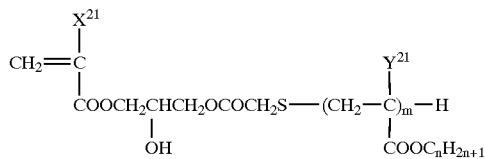

(III-2)

wherein $X^{21}$ and $y^{21}$ are a hydrogen atom or a methyl group, n is from 1 to 22, and m is from 5 to 100.

Specific examples thereof include the followings:

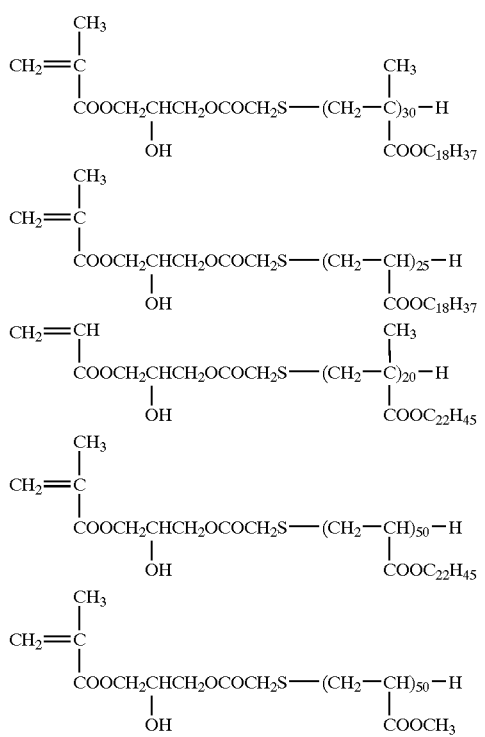

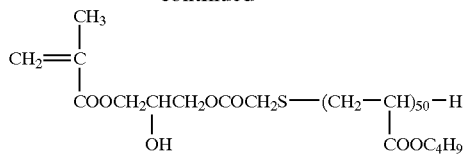

The alkyl (meth)acrylate has, for example, the following structural formula (III-3):

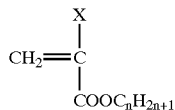

(III-3)

wherein X is a hydrogen atom or a methyl group and n is from 1 to 22 (for example, from 1 to 10).

Specific examples include methyl (meth)acrylate, ethyl (meth)acrylate, propyl (meth)acrylate, n-butyl (meth) acrylate, t-butyl (meth)acrylate, n-octyl (meth)acrylate, 2-ethylhexyl (meth)acrylate, dodecyl (meth)acrylate, cetyl (meth)acrylate, stearyl (meth)acrylate and behenyl (meth) acrylate.

These fluorine-free monomers may be used in admixtures of at least two of them.

In copolymers comprising a fluorine-containing monomer (namely, fluorine-containing (meth)acrylate) and a silicon-containing polymerizable compound, the content of the fluorine-containing (meth)acrylate (A) preferably has a lower limit of 5% by weight, for example, 10% by weight, particularly 20% by weight and an upper limit of 99% by weight, for example, 95% by weight, particularly 80% by weight, based on the total amount of the fluorine-containing monomer and the silicon-containing polymerizable compound. As the proportion of the silicon-containing polymerizable compound in the copolymer becomes larger, feelings in use of cosmetics in which the copolymer is blended, that is, a "sleek feeling" and a "dry feeling" become better and solubility of the copolymer in fluorine-free solvents becomes higher. The amount of the silicon-containing polymerizable compounds (B) preferably has a lower limit of 1% by weight, for example, 5% by weight, particularly 20% by weight, and an upper limit of 95% by weight, for example, 90% by weight, particularly 80% by weight, especially 50% by weight, based on the total amount of the fluorine-containing monomer and the silicon-containing polymerizable compounds. The amount of the fluorine-free monomers (C) which are optionally used is from 0 to 50% by weight, for example, from 1 to 50% by weight, particularly from 2 to 30% by weight, based on the total amount of the fluorine-containing monomers and the silicon-containing polymerizable compounds,.

For improving the feeling in use and imparting functions other than the waterproofing property and the water- and oil-repellency to films, other monomer may be used together. Specific examples of the other monomer include glycidyl (meth)acrylate, cyclohexyl (meth)acrylate, vinyl chloride, vinylidene chloride and (meth)acrylic acid. The amount of the other monomer in a copolymer may be at most 20% by weight, for example, from 0.1 to 10% by weight relative to the copolymer.

When at least one of a hydrophilic group-containing monomer and/or a nitrogen-containing monomer is used as the other monomer, the resulting copolymer has good adsorbability to the hair and is suitable as a copolymer for hair cosmetics.

In the hair cosmetics, a copolymer having repeating units derived from (a) the fluorine-containing (meth)acrylate, (b) the silicon-containing polymerizable compound and (c) the hydrophilic group-containing monomer and/or nitrogen-containing monomer is preferred. The weight ratio of (a):(b):(c) in the copolymer may be 10–90:10–90:0.1–20, preferably 20–80:20–80:1–10.

The Rf group in the fluorine-containing (meth)acrylate particularly preferred from the viewpoint of the feeling in use is a perfluoropolyether.

Examples of the hydrophilic group-containing monomer include (meth)acrylic acid and the aforementioned polyalkyleneglycol (meth)acrylate.

Examples of the nitrogen-containing monomer include (meth)acrylamide, N,N-dimethylacrylamide, (meth)acrylonitrile, N-vinylpyrrolidone, dimethylaminoethyl (meth)acrylate, diethylaminoethyl (meth)acrylate, diacetone acrylamide, trimethylammonium chloride ethyl (meth)acrylate, methacryloyloxyethyttrimethylammonium chloride, 2-hydroxy-3-methacryloyloxypropyltrimethylammonium chloride, and monomers having at least one urethane or urea linkage.

In particular, diacetone acrylamide and the monomers having at least one urethane or urea linkage are preferred.

Examples of the monomers having at least one urethane or urea linkage include bis(acryloyloxyethyl)hydroxyethyl isocyanurate, tris(acryloyloxyethyl) isocyanurate,

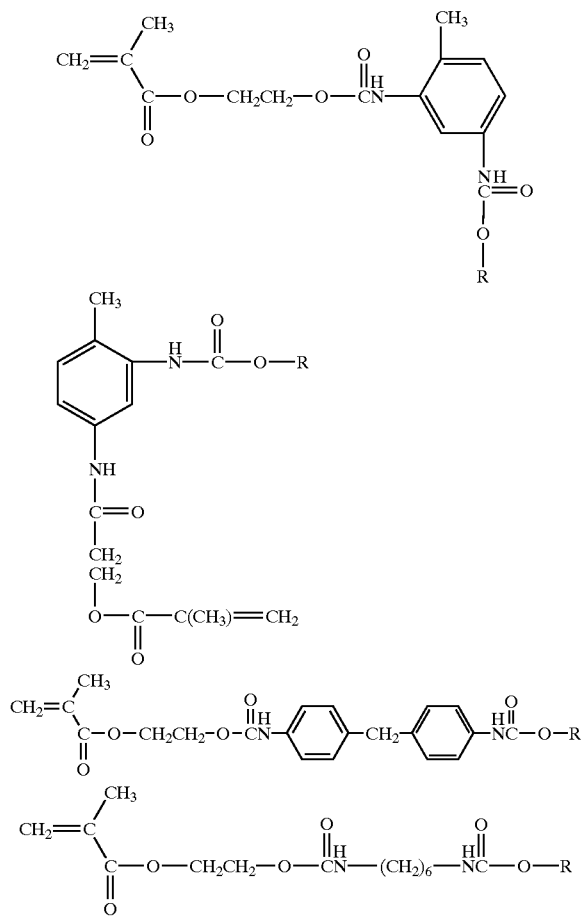

wherein R is an alkyl group having 1 to 22 carbon atoms.

The fluorine-containing copolymer of the present invention can be produced by bulk polymerization, solution polymerization and emulsion polymerization. In the bulk polymerization, a method is adopted in which a mixture of a fluorine-containing monomer and a silicon-containing polymerizable compound is purged by nitrogen, a polymerization initiator is then added, and the mixture is stirred in the range of from 40 to 80° C. for several hours to be polymerized. Alternatively, in the case of the solution polymerization, a mixture of the fluorine-containing monomer and the silicon-containing polymerizable compound is dissolved in a suitable organic solvent in which these monomers can dissolve and then polymerized in the same manner as described earlier. The organic solvent may be a hydrocarbon-based solvent, an ester-based solvent, a ketone-based solvent, an alcohol-based solvent, a silicone-based solvent, a fluorine-containing solvent and the like.

In the case of the emulsion polymerization, the polymerization is carried out in the same manner as described above after emulsifying these monomers in water using a proper emulsifier. In some combinations of a fluorine-containing monomer and a silicon-containing polymerizable compound, a poor compatibility of a fluorine-containing monomer and a silicon-containing polymerizable compound in water results in a poor copolymerizability. In such a case, a method in which a proper auxiliary solvent such as glycols and alcohols is added to improve the compatibility of the monomers is adopted. A hydrophobic group in the emulsifier to be used in the emulsion polymerization may be any of hydrocarbon type, silicon-containing type and fluorine-containing type. As for the ionicity of a hydrophilic group, any of nonionic one, anionic one, cationic one and amphoteric one may be used.

The polymerization initiator may be exemplified by various azo-type ones and peroxides. In the polymerization, a chain transfer agent or a pH modifier may be added. The weight average molecular weight (measured by GPC) of the fluorine-containing copolymer obtained after the polymerization is from 10,000 to 1,000,000, preferably from 20,000 to 300,000.

A fluorine-containing copolymer prepared by solution polymerization or emulsion polymerization may be blended directly in the form of a reaction liquid into cosmetic preparations. Alternatively, the polymer may be dissolved (or dispersed) in solvents (or water) after the isolation of only the polymers.

Although the fluorine-containing copolymer may be an isolated polymer, it is preferable that the copolymer is supplied as a raw material of cosmetics in a form in which it is dissolved or dispersed in water or at least one of hydrocarbon-based solvents, alcohol-based solvents, ester-based solvents, ketone-based solvents, silicone-based solvents and fluorine-containing solvents. The fluorine-containing copolymer is contained in an amount of from 1 to 60% by weight, preferably from 1 to 50% by weight, more preferably from 10 to 40% by weight relative to the total amount [the fluorine-containing copolymer plus (water or a solvent)]. When it is less than 1% by weight, the fluorine-containing copolymer blended in a cosmetic preparation is too little, imparting insufficient waterproofing property or water- and oil-repellency. When it is more than 60% by weight, the stability as a raw material is deteriorated.

Hair cosmetics may contain the copolymer of the present invention in an amount of from 1 to 99% by weight, preferably from 2 to 50% by weight.

Examples of the hydrocarbon-based solvents include n-hexane, n-heptane, n-octane, n-nonane, n-decane, n-undecane, n-dodecane, isohexane, isoheptane, isooctane, isononane, isodecane, isoundecane, isododecane, cyclohexane, methylcyclohexane, cyclopentane, methylcyclopentane, liquid paraffin, isoparaffin, toluene, benzene and xylene.

Examples of the alcohol-based solvents include ethanol and isopropyl alcohol.

Examples of the ester-based solvents include butyl acetate, ethyl acetate, amyl acetate and acyl acetate.

Examples of the ketone-based solvents include methyl ethyl ketone, methyl isobutyl ketone and acetone.

Examples of the silicone-based solvents include hexamethylcyclotrisiloxane (that is, a cyclic silicone trimer), octamethylcyclotetrasiloxane (that is, a cyclic silicone tetramer), decamethylcyclopentasiloxane (that is, a cyclic silicone pentamer), dodecamethylcyclohexasiloxane (that is, a cyclic silicone hexamer), dimethylpolysiloxane, methylphenylpolysiloxane and a dimethylpolysiloxane/methyl(polyoxyethylene)sitoxane/ethyl(polyoxypropylene) siloxane copolymer.

Examples of the fluorine-containing solvents include hydrofluorocarbon (HFC), hydrofluoroether (HFE), fluoroether, fluorocarbon (FC) and nitrogen-containing fluorocarbon.

The HFC may be 1,1,1,2,2,3,4,5,5,5-decafluoropentane (HFC-4310), benzotrifluoride, m-xylene hexafluoride and the like.

The HFE may be represented by the general formula:

wherein n is a number of from 1 to 12, m is a number of from 0 to 25, 1 is a number of from 0 to 11, m+1=2n+1, x is a number of from 1 to 12, y is a number of from 0 to 25, z is a number of from 0 to 11 and y+z=2x+1, provided that m and y are not simultaneously zero and 1 and z are not simultaneously zero.

The HFE may be, for example, $C_4F_9OCH_3$ and $C_4F_9OC_2H_5$.

The fluoroether may be represented by the general formula:

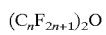

wherein n is a number of from 3 to 5.

The fluoroether may be, for example, $(C_3F_7)_2O$ and $(C_4F_9)_2O$.

Examples of the FC include perfluorohexane, perfluorooctane, perfluorononane, perfluorobenzene, perfluorotoluene, perfluoroxylene, perfluorodecalin and perfluoromethyldecalin.

The nitrogen-containing fluorocarbon may be represented by the general formula:

wherein n is a number of from 1 to 5.

The nitrogen-containing fluorocarbon may be, for example, perfluorotripropylamine and perfluorotributylamine.

These solvents may be used either alone or in admixtures. Solvents having a property to evaporate easily at the skin temperature (about 30° C.) are preferred since they can provide a cool feeling during their volatilization and can form films on the skin easily. Particularly, octamethylcyclotetrasiloxane (that is, a cyclic silicone tetramer), decamethylcyclopentasiloxane (that is, a cyclic silicone pentamer), dimethylpolysiloxanes having viscosities of not greater than 10 cSt, which are silicone-based solvents, and isoparaffin, which is a hydrocarbon, are preferably used. In the case of using the fluorine-containing solvent, use of $C_4F_9OCH_3$, $C_4F_9OC_2H_5$, $C_4F_9OC_3H_7$ or $C_4F_9OC_4H_9$, which are HFEs, is most desirable. This type of solvents are volatile and soluble in many solvents and oils widely used for cosmetics. They also have high solubilities of fluorine-containing polymers.

The cosmetic of the present invention contains 0.1 to 30% by weight of the fluorine-containing copolymer as a main ingredient and may contain at least 0.1% by weight of a fluorine compound-treated powder and/or a fluorine-containing oil.

Moreover, the cosmetics of the present invention may compatibilize or disperse the fluorine compound-treated powder and/or the fluorine-containing oil in a non-fluorine compound (for example, a fluorine-free solvent) using the fluorine-containing copolymer as a compatibilizer or a dispersing agent.

The fluorine-containing oil may be a perfluoropolyether, a hydrofluoroether or a compound represented by the general formula:

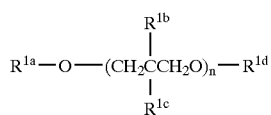

wherein $R^{1a}$ and $R^{1d}$ represent a hydrogen atom or a partly or completely fluorinated aliphatic group having 1 to 20 carbon atoms, $R^{1b}$ and $R^{1c}$ represent a hydrogen atom, an aliphatic group having 1 to 20 carbon atoms or a partly or completely fluorinated aliphatic group having 1 to 20 carbon atoms, provided that at least one of $R^{1a}$ to $R^{1d}$ is a partly or completely fluorinated aliphatic group having 1 to 20 carbon atoms, and n is a number of from 1 to 20, or by the general formula:

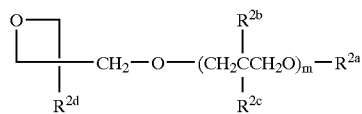

wherein $R^{2a}$ is a hydrogen atom or a partly or completely fluorinated aliphatic group having 1 to 20 carbon atoms, $R^{2b}$, $R^{2c}$ and $R^{2d}$ are an aliphatic group having 1 to 20 carbon atoms or a partly or completely fluorinated aliphatic group having 1 to 20 carbon atoms, provided that at least one of $R^{2a}$ to $R^{2d}$ is a partly or completely fluorinated aliphatic group having 1 to 20 carbon atoms, and m is a number of from 1 to 20.

Raw materials to be used for the cosmetics in which the fluorine-containing copolymer of the present invention is blended are not particularly restricted as long as they are generally used for cosmetics.

For example, powders may be exemplified by inorganic powders such as talc, kaolin, mica, mica titanium, titanium oxide, iron oxide, magnesium oxide, zinc monooxide, zinc dioxide, heavy or light calcium carbonate, calcium secondary phosphate, aluminum hydroxide, barium sulfate, silica, alumina, silica gel, carbon black, antimony oxide, magnesium silicate aluminate, magnesium metasilicate aluminate and synthesized mica; and organic powders such as protein powder, fish scale foil, metal soap, polyvinyl chloride, nylon-12, microcrystalline fiber powder, tar pigment and lake. These may be ones either untreated or treated with a silicone or a fluorine compound. For example, the powder may be a fluorine compound-treated powder.

Furthermore, examples other than powders include solid or semi-solid fats such as vaseline, lanoline, ceresin, microcrystalline wax, carnauba wax, candelilla wax, higher fatty acids and higher alcohols; liquid fats such as squalane, liquid paraffin, ester oil, diglyceride, triglyceride and silicone oil; fluorine-containing oils such as perfluoropolyether, perfluorodecalin and perfluorooctane; water-soluble or oil-soluble polymers, surfactants, colorants such as organic dyes, ethanol, antiseptics, antioxidants, colorant, thickeners, pH modifiers, perfumes, ultraviolet absorbers, humectants, blood circulation promoters, cold feeling agents, antiperspirants, germicides and skin activators.

The cosmetic of the present invention can be produced in accordance with conventional methods and can be used as a finishing cosmetic such as foundation, face powder, cheek color, eye color, mascara, eyeliner and nail color; basic cosmetics such as a milky lotion and cream; hair cosmetics such as shampoo and rinse.

The copolymer for cosmetics of the present invention can be used for improving the following drawbacks of fluorine compound-treated powders:

They have poor affinities with fluorine-free raw materials.

They have poor feelings in use, such as poor spread and poor adhesion.

They rise in the form of dust in the air during the production of cosmetics.

They are poor in dispersibility in fluorine-free solvents.

The fluorine compound-treated powder to be treated with the copolymer of the present invention may be a powder treated with a fluorine-containing phosphate ester such as a fluorine-containing phosphate ester represented by the general formula:

[Rf—A—O]$_n$PO(OM)$_{3-n}$ wherein Rf represents a polyfluoroalkyl or perfluoropolyether group having 6 to 16 carbon atoms, A represents an alkylene group having 1 to 4 carbon atoms, or

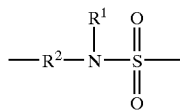

$$-R^2-N(R^1)-\overset{O}{\underset{O}{S}}-$$

wherein $R^1$ is an alkyl group having 1 to 4 carbon atoms and $R^2$ is an alkylene group having 1 to 4 carbon atoms, or

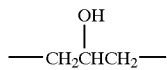

$$-CH_2CH(OH)CH_2-$$

M represents a hydrogen atom, a metal atom, ammonium or substituted ammonium and n represents a number of from 1 to 3.

An example is a fluorine compound-treated powder obtained by treating powders with 3 to 7% by weight, relative to the powders, of a perfluoroalkyl phosphate ester diethanolamine salt.

Examples of the fluorine compound-treated powder include those obtained by treating powders, for example, inorganic or organic powders, with fluorine compounds. At least two powders may be mixed when they are surface-treated with the copolymer. Moreover, at least two treated powders may be mixed also when they are blended to cosmetics.

The copolymer for cosmetics is made to be adhered to the surface of a fluorine compound-treated powder by a wet method or a dry method, and the wet method is preferred for uniform surface treatment. For example, a fluorine compound-treated powder is mixed in a solution prepared by diluting either the copolymer itself or a solution of the copolymer with an organic solvent and stirred until the fluorine compound-treated powder gets wet uniformly with the organic solvent solution at room temperature or under heating. For the stirring in the above procedure, a stirring device is used, for example, a Henschel mixer, a vibratory ball mill, a rotary ball mill, a supermixer and a planetary mixer. In stirring in a laboratory scale, a juicer for home use may be employed. The concentration of the copolymer in a solution in an organic solvent is not particularly limited, but is adjusted so that the viscosity does not become too high during the stirring in the mixing of powder. After the stirring, the organic solvent is removed under a vacuum condition or by heating and the treated powder is dispersed uniformly by means of the aforementioned stirring device. In stirring in a laboratory scale, a juicer for home use or a speed cutter may be used.

The copolymer for cosmetics of the present invention can also be used for the improvement of the waterproofing property and the oil-repellency of a silicone-treated powder. Examples of the silicone-treated powder to be treated include one which has been treated with methylhydrogenpolysiloxane by a wet method and one which has been treated with 1,3,5,7-tetramethylcyclotetrasiloxane by a chemical gas-phase vapor deposition method. Examples of a powder to be treated for the silicone-treated powder include talc, kaolin, mica, mica titanium, titanium oxide, iron oxide and zinc oxide, which are widely used in cosmetics, as in the aforementioned fluorine-treated powder. When the silicone-treated powder is surface-treated with the copolymer, at least two silicone-treated powders may be mixed. Furthermore, also when the treated powder is incorporated into the cosmetics, at least two silicone-treated powders may be mixed.

Although the copolymer for cosmetics is adhered to the surface of the silicone-treated powder by the wet method or the dry method as in the aforementioned fluorine-treated powder, the wet method is preferable for uniform surface-treatment.

In the powder coated with the copolymer of the present invention, the amount of the copolymer may be from 0.1 to 50% by weight, for example, from 1 to 30% by weight, based on the coated powder.

In the present invention, proper chemicals to improve the feeling in use may, if needed, be used together in the surface-treatment. Examples of the chemicals to improve the feeling in use include lecithin, N-mono-long-chain-acyl basic amino acids, silicone, chitosan, collagen and wax.

Heretofore, since fluorine-containing oils typified by perfluoropolyether have poor affinities with fluorine-free raw materials, they are difficult to be blended into cosmetics. After the intensive study for overcoming the above problem, the present invention facilitates the blending of the fluorine-containing oils into cosmetics by emulsifying the fluorine-containing oils in fluorine-free solvents such as silicone-based solvents, hydrocarbon-based solvents, ester-based solvents and ketone-based solvents by using the fluorine-containing (meth)acrylate copolymers having specific composition as emulsifiers to form fluorine-containing oil/fluorine-free solvent type nonaqueous emulsions.

The present invention provides a cosmetic comprising a nonaqueous emulsion obtained by emulsifying a fluorine-containing oil in a fluorine-free solvent using a copolymer for cosmetics as a emulsifier, wherein the fluorine-free solvent is any of a silicone-based solvent, a hydrocarbon-based solvent, an ester-based solvent and a ketone-based solvent, wherein the fluorine-containing oil is a perfluoropolyether, a hydrofluoroether, a compound represented by the general formula:

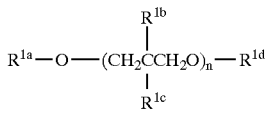

wherein $R^{1a}$ and $R^{1d}$ represent a hydrogen atom or a partly or completely fluorinated aliphatic group having 1 to 20 carbon atoms, $R^{1b}$ and $R^{1c}$ represent a hydrogen atom, an aliphatic group having 1 to 20 carbon atoms or a partly or completely fluorinated aliphatic group having 1 to 20 carbon atoms, provided that at least one of $R^{1a}$ to $R^{1d}$ is a partly or completely fluorinated aliphatic group having 1 to 20 carbon atoms, and n is a number of from 1 to 20, or by the general formula:

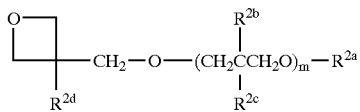

wherein $R^{2a}$ is a hydrogen atom or a partly or completely fluorinated aliphatic group having 1 to 20 carbon atoms, $R^{2b}$, $R^{2c}$ and $R^{2d}$ are an aliphatic group having 1 to 20 carbon atoms or a partly or completely fluorinated aliphatic group having 1 to 20 carbon atoms, provided that at least one of $R^{2a}$, to $R^{2d}$ is a partly or completely fluorinated aliphatic group having 1 to 20 carbon atoms, and m is a number of from 1 to 20.

The amount of the emulsifier may be from 1 to 50 parts by weight, for example, from 5 to 20 parts by weight, relative to 100 parts by weight of the fluorine-containing oil. The amount of the fluorine-free oil may be from 50 to 10,000 parts by weight, for example, from 100 to 1,000 parts by weight, relative to 100 parts by weight of the fluorine-containing oil.

In general, in the case wherein a large amount of oil-soluble polymer is blended into cosmetics, it is blended in the form of solution in a volatile solvent. This is because an oil-soluble polymer is difficult to be converted into preparations since it is a solid or an elastic rubbery material. A volatile solvent typified by cyclic silicone and isoparaffin has a superior ability of dissolving the oil-soluble polymer and can impart superior functions to cosmetics, but it shows very strong skin irritation and can not be used in cosmetics for sensitive skins which is required to have low irritability. Therefore, a paste-form oil-soluble polymer which is easily converted into preparations has been demanded. The "paste-form" used herein means that a material has less fluidity at room temperature and has such rheological properties that it can be easily applied to the skin with a hand.

Although also in the present invention, most of the copolymers are solid or rubbery, fluorine-containing (meth)acrylate copolymers having specific compositions have been found to be in the paste-form after the intensive studies for overcoming the aforementioned problems.

The present invention also provides a cosmetic comprising a copolymer comprising a fluorine-containing (meth)acrylate and a silicon-containing polymerizable compound, characterized in that the copolymer is in a paste-form and contains the fluorine-containing (meth)acrylate and the silicon-containing polymerizable compound at a weight ratio of from 3/7 to 7/3 and in that no volatile solvent is blended.

The composition of the copolymer may be a weight ratio of the fluorine-containing (meth)acrylate to the silicon-containing polymerizable compound of from 3/7 to 7/3, for example, from 4/6 to 6/4. The addition of a proper amount of a solid or rubbery polymer to the copolymer can vary the properties of the paste. The amount of the paste-form copolymer is from 1 to 100% by weight, for example, from 2 to 80% by weight relative to the whole cosmetic.

The present invention may use raw materials which is conventionally used for cosmetics except that the paste-form copolymer is contained as an essential ingredient and no volatile solvent is present. For example, in addition to the copolymer, at least one of a powder, a high-boiling oil, a solid oil, water, a water-soluble polymer, an emulsifier and a humectant may be blended.

The selection of fluorine-containing copolymers produced by polymerizing the fluorine-containing (meth)acrylate and the silicon-containing polymerizable compound as essential components results in cosmetics satisfying the waterproofing property and water- and oil-repellency derived from the fluorine-containing (meth)acrylate and the waterproofing property, the water-repellency and the feelings in use (such as the "sleek feeling" and the "dry feeling") derived from the silicon-containing polymerizable compound. Furthermore, copolymerizing the silicon-containing polymerizable compound facilitates the copolymer to dissolve in silicone oils widely used in cosmetics. When the copolymer is blended into cosmetic preparations in which large amounts of fluorine-containing raw materials and silicone-containing raw materials are blended, the copolymer serves as a compatibilizer and improves stability of the preparations.

Moreover, the selection of a fluorine-containing copolymer in which alkyl (meth)acrylate, wherein the alkyl group preferably has 1 to 4 carbon atoms, or an alkyl (meth) acrylate macromonomer, wherein the alkyl group preferably has 1 to 22 carbon atoms, is polymerized in addition to the fluorine-containing (meth)acrylate and the silicon-containing polymerizable compound can improve the solubility of the copolymer in hydrocarbon-based solvents, ester-based solvents and ketone-based solvents. In particular, the use of the alkyl (meth)acrylate macromonomer results in graft copolymers comprising fluorine-containing (meth)acrylate segments, silicon-containing polymerizable compound segments and alkyl (meth)acrylate macromonomer segments, whereby improving the solubility and exhibiting a high waterproofing property and high water- and oil-repellency at low fluorine concentrations. When the copolymer is blended to cosmetic preparations in which the fluorine-containing raw materials, the silicone-containing raw materials and the hydrocarbon-based, ester-based or ketone-based solvents, the copolymer serves as a compatibilizer and improves the stability of the preparations.

The selection of a fluorine-containing copolymer comprising a polyalkyleneglycol (meth)acrylate prevents make-up from coming off easily even under the environment where sweat and sebum are present together. Generally, the surface of a fluorine-containing copolymer which does not contain any hydrophilic monomer repels oil under dry conditions, but gets wet with oil when water is present together with oil [see "Surface property and application of fluoroalkyl acrylate polymers", Motonobu Kubo, SURFACE, 33, 185 (1995)]. To prevent this, a hydrophilic monomer, particularly polyethyleneglycol (meth)acrylate, may be copolymerized. The amounts of sweat and sebum on the skin vary depending on the external environment. Fluorine-containing copolymers containing polyethyleneglycol (meth)acrylates show the water- and oil-repellency under any environment. However, the use of these monomers tends to cause some deterioration of the waterproofing property.

PREFERRED EMBODIMENT OF THE INVENTION

Examples of the present invention will be described, but Examples do not limit the present invention.

PREPARATIVE EXAMPLE 1

In a four-neck flask equipped with a reflux condenser, a nitrogen introduction tube, a thermometer and a stirrer, were placed 20 g of $CH_2=CHCOO(CH_2)_2(CF_2CF_2)_nCF_2CF_3$ (hereinafter referred to as "FA") (a mixture of compounds wherein n is 3, 4 and 5 in a weight ratio of 5:3:1), 20 g of a side-chain mercapto-modified silicone:

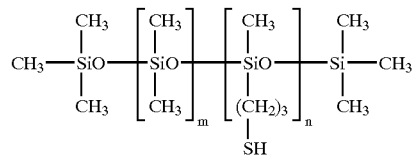

wherein m is from 10 to 200 and n is from 1 to 10 (KF-2001 manufactured by Shin-Etsu Chemical Co., Ltd.) (hereinafter referred to as "Si-SH") and 158 g of toluene, which were heated up to 60° C. and stirred for 30 minutes under nitrogen flow. To this mixture was added 2 g of t-butyl peroxypivalate (trade name: Perbutyl PV, manufactured by NOF Corp.) and polymerization was carried out for 6 hours. By the gas chromatography analysis of the remaining FA in the reaction liquid, the polymerization conversion of FA was found to be 95%. A precipitation was obtained from the resulting reaction liquid by using methanol and was vacuum-dried to isolate a FA/Si-SH (=5/5 wt.) copolymer. The measurement of a molecular weight of the resulting FA/Si-SH copolymer by GPC revealed that the weight average molecular weight was 20,000 (in terms of polystyrene).

PREPARATIVE EXAMPLE 2

By polymerization in the same manner as in Preparative Example 1 except that 20 g of the monomer in Preparative Example 1, Si-SH, was replaced by 10 g of Si-SH and 10 g of n-butyl acrylate (BA), an FA/Si-SH/BA (=5/2.5/2.5 wt.) copolymer was produced. The copolymer had a weight average molecular weight of 35,000.

PREPARATIVE EXAMPLE 3

By polymerization in the same manner as in Preparative Example 1 except that 20 g of the monomer in Preparative Example 1, Si-SH, was replaced by 20 g of both-ends-mercapto-modified silicone:

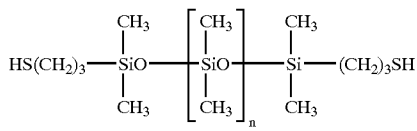

wherein n is from 10 to 20 (X-22-167B manufactured by Shin-Etsu Chemical Co., Ltd.) (hereinafter referred to as "Si-DSH"), an FA/Si-DSH (=5/5 wt.) copolymer was produced. The copolymer had a weight average molecular weight of 25,000.

PREPARATIVE EXAMPLE 4

By polymerization in the same manner as in Preparative Example 1 except that 20 g of the monomer in Preparative Example 1, Si-SH, was replaced by 10 g of Si-DSH and 10 g of BA, an FA/Si-DSH/BA (=5/2.5/2.5 wt.) copolymer was produced. The copolymer had a weight average molecular weight of 22,000.

PREPARATIVE EXAMPLE 5

By polymerization in the same manner as in Preparative Example 1 except that 20 g of the monomer in Preparative Example 1, Si-SH, was replaced by 10 g of azo group-containing silicone:

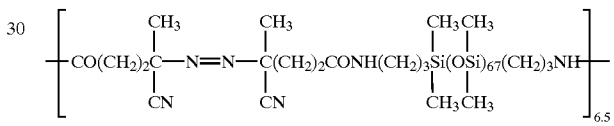

(VPS-0501 manufactured by Wako Pure Chemical Industries, Ltd.) (hereinafter referred to as "Azo-Si") and 10 g of BA, an FA/Azo-Si/BA (=5/2.5/2.5 wt.) copolymer was produced. The copolymer had a weight average molecular weight of 24,000.

PREPARATIVE EXAMPLE 6

By polymerization in the same manner as in Preparative Example 1 except that 20 g of the monomer in Preparative Example 1, Si-SH, was replaced by 20 g of 3-methacryloxypropyltrimethoxysilane:

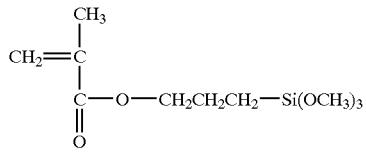

(Sila-Ace S710 manufactured by Chisso Corp.) (hereinafter referred to as "TMS-MA"), an FA/TMS-MA (=5/5 wt.) copolymer was produced. The copolymer had a weight average molecular weight of 21,000.

EXAMPLE 1 AND COMPARATIVE EXAMPLE 1

The copolymers produced in Preparative Examples 1, 2, 3, 4, 5 and 6 were dissolved in cyclic silicone pentamer (decamethylcyclopentasiloxane) or in isoparaffin (Isopar G manufactured by Exxon Chemical Corp.) so that the concentration of the polymers was 5% by weight. The interfacial tensions between these solutions (the concentrations of the copolymers: 5 wt % in fluorine-free solvents) and perfluoropolyether (Demnum S-20 manufactured by Daikin Industries, Ltd.) were measured by a spinning drop method (a measuring device: Spinning Drop Tensiometer SITE-04 manufactured by Krüss GmbH). As Comparative Example, interfacial tensions were measured in a similar manner using a fluorine-free acryl-silicone copolymer [KP-545 manufactured by Shin-Etsu Chemical Co., Ltd. (polymer composition: Si-MM/methyl methacrylate (MMA)/butyl methacrylate (BMA)/2-ethylhexyl acrylate(2EHA)=50/35/7.5/7.5 wt.)] and a fluorine-modified silicone (FS-1265 manufactured by Toray Dow Corning). The results are shown in Table 1.

Si-MM in the acryl-silicone copolymer is a silicone macromonomer represented by the formula:

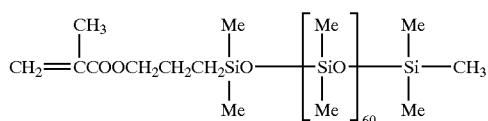

wherein Me is a methyl group.

fluorine-free acryl-silicone copolymer and fluorine-modified silicone FS-1265 used in Comparative Example 1 were also subjected to the same measurements. The results are shown in Table 2. The copolymers of the present invention showed higher contact angles than those of the Comparative Example 2.

TABLE 2

| | | Contact angle of FA copolymer (°) | | |
|---|---|---|---|---|
| Silicon-containing compound | Preparative Example | Composition of copolymer | Water | Liquid paraffin |
| Si—SH | 1 | FA/Si—SH = 5/5 wt. | 121 | 82 |
| | 2 | FA/Si—SH/BA = 5/2.5/2.5 wt. | 113 | 95 |
| Si—DSH | 3 | FA/Si—DSH = 5/5 wt. | 120 | 81 |
| | 4 | FA/Si—DSH/BA = 5/2.5/2.5 wt. | 110 | 93 |
| Azo-Si | 5 | FA/Azo-Si/BA = 5/2.5/2.5 wt. | 111 | 92 |
| TMS—MA | 6 | FA/TMS—MA = 5/5 wt. | 121 | 80 |
| Comparative Example 2 | Acryl-silicone copolymer | Si—MM/MMA/BMA/2EHA = 50/35/7.5/7.5 wt. | 101 | 41 |
| Fluorine-modified silicone | | FS-1265 (Substituent: —CH$_2$CH$_2$CF$_3$) | 83 | 32 |

TABLE 1

| | | | | Interfacial tension (mN/m) | | |
|---|---|---|---|---|---|---|
| Silicon-containing compound | Copolymer | Composition of copolymer | Cyclic silicone pentamer | Ratio of interfacial tensions (%) | Isoparaffin | Ratio of interfacial tensions (%) |
| | — | No copolymer was blended | 5.43 | — | 5.58 | — |
| Si—SH | Preparative Example 1 | FA/Si—SH = 5/5 wt. | 2.55 | 47 | 1.83 | 33 |
| | Preparative Example 2 | FA/Si—SH/BA = 5/2.5/2.5 wt. | 1.55 | 29 | 1.73 | 31 |
| Si-DSH | Preparative Example 3 | FA/Si-DSH = 5/5 wt. | 2.78 | 51 | 1.72 | 31 |
| | Preparative Example 4 | FA/Si-DSH/BA = 5/2.5/2.5 wt. | 1.52 | 28 | 1.22 | 22 |
| Azo-Si | Preparative Example 5 | FA/Azo-Si/BA = 5/2.5/2.5 wt. | 2.22 | 41 | 1.77 | 32 |
| TMS-MA | Preparative Example 6 | FA/TMS-MA = 5/5 wt. | 3.56 | 66 | 3.15 | 56 |
| Comparative Example 1 | Acryl-silicone copolymer | Si-MM/MMA/BMA/2EHA = 50/35/7.5/7.5 wt. | 5.44 | 100 | 5.49 | 98 |
| | Fluorine-modified silicone | FS-1265 (Substituent: —CH$_2$CH$_2$CF$_3$) | 5.44 | 100 | 5.62 | 101 |

Blending the copolymers of the present invention into the fluorine-free solvents decreased interfacial tensions to 20 to 60% of those detected when nothing was blended. This attests the fact that the copolymers are adsorbed on the interfaces between the perfluoropolyether and the fluorine-free solvent. On the other hand, there was no decrease in interfacial tension in Comparative Example 1. This shows that the fluorine-free acryl-silicone copolymer and the fluorine-modified silicone were only dissolved in the fluorine-free solvents and had no abilities to be adsorbed on the interfaces.

EXAMPLE 2 AND COMPARATIVE EXAMPLE 2

The copolymers produced in Preparative Examples 1, 2, 3, 4, 5 and 6 were dissolved in HCFC-225 (CF$_3$CF$_2$CHCl$_2$) so that the concentration of the polymers was 5% by weight and were formed into films on glass substrates by a cast method. The contact angles of water or liquid paraffin on these coating films of the copolymers were measured. The

EXAMPLE 3 AND COMPARATIVE EXAMPLE 3

10 g of a perfluoropolyether (Demnum S-20 manufactured by Daikin Industries, Ltd.) and 20 g of a 5% by weight solution of the copolymer obtained in Preparative Examples 1, 2, 3, 4, 5 or 6 in cyclic silicone pentamer (decamethylcyclopentasiloxane) or isoparaffin were emulsified with an ultrasonic homogenizer for 1 minute. The copolymers produced in Preparative Examples 1, 2, 3, 4, 5 and 6 resulted in stable microemulsions having a particle size of from about 200 to 300 nm. However, in Comparative Example 3 [either a fluorine-free acryl-silicone copolymer (KP-545 manufactured by Shin-Etsu Chemical Co., Ltd. (polymer composition: Si-MM/methyl methacrylate/butyl methacrylate/2-ethylhexyl acrylate=50/35/7.5/7.5 wt.)) or fluorine-modified silicone FS-1265 was used as a copolymer], no emulsion was formed.

In the following Examples and Comparative Examples, cosmetics were prepared using mixture powders shown in Table 3. The fluorine-treated powders (1) to (6) were those obtained by treating untreated powders with 5% by weight, based on the untreated powders, of perfluoroalkylethyl phosphate ester diethanol amine salt. The silicone-treated powders (7) to (9) were those obtained by treating untreated powders with 2% by weight, based on the untreated powders, of methylhydrogenpolysiloxane.

TABLE 3

Composition of mixture powder

| Type of raw material | % by weight |
| --- | --- |
| (1) Fluorine-treated titanium oxide | 8.0 |
| (2) Fluorine-treated yellow iron oxide | 0.9 |
| (3) Fluorine-treated red iron oxide | 0.3 |
| (4) Fluorine-treated black iron oxide | 0.3 |
| (5) Fluorine-treated talc | 28.7 |
| (6) Fluorine-treated sericite | 31.5 |
| (7) Silicone-treated talc | 3.8 |
| (8) Silicone-treated sericite | 19.1 |
| (9) Silicone-treated mica | 7.4 |

Make-up lastingness (derived from the water- and oil-repellency of a film), feelings in use (the "sleek feeling" and the "dry feeling") and a waterproofing properly were evaluated according to the following criteria:

⊚: Very good

○: Good

Δ: Average

X: Poor

X X: Very poor

The evaluation was done by five panelists specialized in functional evaluation. The average of their evaluations was taken as the result. As for the waterproofing property, films formed by evenly coating materials on polyester films and leaving them for one day were used as test samples. The waterproofing properties were evaluated from contact angles of water on the films after immersing the films in water for one hour and then leaving them in the air for one day.

Cases wherein a contact angle is from 110 to 130° are indicated by "⊚", those wherein a contact angle is from 90 to 109° are indicated by "○", those wherein a contact angle is from 60 to 89° are indicated by "Δ", those wherein a contact angle is from 30 to 59° are indicated by "X ", and those wherein a contact angle is less than 29° are indicated by "X X".

EXAMPLE 4 AND COMPARATIVE EXAMPLE 4

The fluorine-treated powders (1) to (6), constituents of the mixture powders shown in Table 3, were surface-treated with the FA/Si-SH (=5/5 wt.) copolymer of Preparative Example 1by the following procedure. 40 g of a mixture of the fluorine-treated powders (1) to (6), 2 g of the FA/Si-SH copolymer and 100 g of toluene were mixed with a juicer mixer for 30 seconds. The resulting mixture was placed in an aluminum vat and dried at 60° C. overnight. After drying, the residue was ground with a speed cutter to give a fluorine-treated powder surface-treated with the FA/Si-SH copolymer.

In Comparative Example 4, a fluorine-treated powder was surface-treated with a fluorine-free acryl-silicone copolymer which was the same as in Comparative Example 1, in place of the FA/Si-SH (=5/5 wt.) of Preparative Example 1.

Powdery foundations were produced using 89.8% by weight of mixture powder containing 69.7% by weight of the fluorine-treated powder which had been surface-treated with the aforementioned FA/Si-SH copolymer or fluorine-free acryl-silicone copolymer, 0.1% by weight of paraoxybenzoate ester, 10% by weight of dimethylpolysiloxane and 0.1% by weight of a perfume.

The ingredients (1) or (2) and (3) were mixed and ground with an atomizer and then transferred to a Henschel mixer. To the mixture, the ingredients (4) and (5) were added and mixed intimately. The resultant was placed in a mold and press molded to give powdery foundations. The make-up lastingness, waterproofing property and feelings in use of the powdery foundations were evaluated. The results are shown in Table 4.

TABLE 4

Powdery foundation

| Type of raw material | Example 4 | Comparative Example 4 |
| --- | --- | --- |
| (1) Copolymer-treated mixture powder | 89.8 | 0 |
| (2) Fluorine-free copolymer-treated mixture powder | 0 | 89.8 |
| (3) Paraoxybenzoate ester | 0.1 | 0.1 |
| (4) Dimethylpolysiloxane | 10.0 | 10.0 |
| (5) Perfume | 0.1 | 0.1 |
| Make-up lastingness | ⊚ | Δ |
| Water-proofing property | ⊚ | ○ |
| Feelings in use | ⊚ | ○ |

The values in the table are indicated by "% by weight".

EXAMPLES 5 to 9

The procedure of Example 4 was repeated except that the FA/Si-SH (=5/5 wt.) copolymer used in Example 4 was replaced by the copolymers of Preparative Example 2 (Example 5), of Preparative Example 3 (Example 6), of Preparative Example 4 (Example 7), of Preparative Example 5 (Example 8), and of Preparative Example 6 (Example 9), respectively. In Examples 5 to 9, all of the make-up lastingness, the waterproofing property and the feeling in use were ⊚.

EXAMPLE 10 AND COMPARATIVE EXAMPLE 5

Nail colors were prepared in the compositions shown in Table 5. The ingredients (1) to (10) were mixed and stirred in a dispersion mill. To the mixture, the ingredient (11) or (12) was added and further mixed and stirred to give nail colors. The powder of the ingredient (11) was surface-treated with the FA/Si-SH/BA (=5/2.5/2.5 wt) copolymer of Preparative Example 2 in the same manner as Example 4. In Comparative Example 5 was used a fluorine-treated powder which had been surface-treated with, in place of the FA/Si-SH/BA (=5/2.5/2.5 wt) copolymer of Preparative Example 2, the fluorine-free acryl-silicone copolymer which was the same as in Comparative Example 1. The dispersibilities were evaluated according to the following criteria:

⊚: Very good
○: Good
Δ: Average
X: Poor
X X: Very poor

TABLE 5

Nail color

| Type of raw material | Example 10 | Comparative Example 5 |
|---|---|---|
| (1) Nitrocellulose | 9 | 9 |
| (2) Alkyd resin | 9 | 9 |
| (3) Acetyltributyl citrate | 3 | 3 |
| (4) dl-Camphor | 0.5 | 0.5 |
| (5) Organic Bentonite | 1.5 | 1.5 |
| (6) Isopropyl alcohol | 5 | 5 |
| (7) Ethyl acetate | 10 | 10 |
| (8) Butyl acetate | 25 | 25 |
| (9) Butanol | 4 | 4 |
| (10) Toluene | 31 | 31 |
| (11) Fluorine-treated mica titanium surface-treated with FA/Si—SH/BA (= 5/2.5/2.5 wt.) copolymer | 2 | — |
| (12) Fluorine-treated mica titanium surface-treated with fluorine-free acryl-silicone copolymer | — | 2 |
| Dispersibility | ⊚ | X |

The values in the table are indicated by "% by weight".

EFFECT OF THE INVENTION

The copolymer for cosmetics of the present invention can be easily incorporated into conventional cosmetic preparations. The cosmetics in which the copolymer is blended therein can form films excellent in the waterproofing property, water- and oil-repellency, feeling in use and safety after the application to the skin.

Moreover, the copolymer for cosmetics serves as a compatibilizer for fluorine-containing raw materials and fluorine-free raw materials and has an effect of stabilizing cosmetic preparations. Furthermore, the surface treatment of fluorine compound-treated powders with the copolymer for cosmetics can improve the following drawbacks of the fluorine compound-treated powders:

They have poor affinities with fluorine-free raw materials.
They have poor feeling in use, such as poor spread and poor adhesion.
They rise in the form of dust in the air during the production of cosmetics.
They are poor in dispersibility in fluorine-free solvents.

What is claimed is:

1. A copolymer comprising:
   (A) 5 to 99 parts by weight of repeating units derived from a fluorine-containing (meth)acrylate, and
   (B) 95 to 1 parts by weight of repeating units derived from at least one silicon-containing polymerizable compound selected from the group consisting of a mercapto-modified silicone, an azo group-containing silicone and a polymerizable silane.

2. The copolymer according to claim 1, further comprising (C) 1 to 50 parts by weight of repeating units derived from at least one fluorine-free monomer selected from the group consisting of a polyalkyleneglycol (meth)acrylate, an alkyl (meth)acrylate macromonomer and an alkyl (meth)acrylate, in addition to the repeating units (A) and (B).

3. The copolymer according to claim 1, wherein the fluorine containing (meth)acrylate is a compound represented by formula (I-1):

(I-1)

wherein Rf is a polyfluoroalkyl or perfluoropolyether group having 6 to 16 carbon atoms,
A is an alkylene group having 1 to 4 carbon atoms or

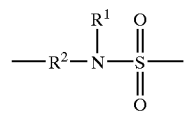

wherein $R^1$ is an alkyl group having 1 to 4 carbon atoms and $R^3$ is an alkylene group having 1 to 4 carbon atoms, or

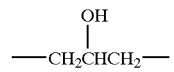

and X is a hydrogen atom or a methyl group, or
a fluorine-containing (meth)acrylate macromonomer represented by formula (I-2):

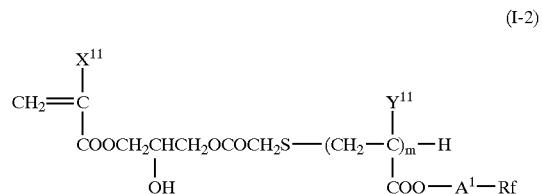
(I-2)

wherein Rf is a polyfluoroalkyl or petfluoropolyether group having 6 to 16 carbon atoms,
$A^1$ is an alkylene group having 1 to 4 carbon atoms or

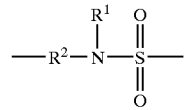

wherein $R^1$ is an alkyl group having 1 to 4 carbon atoms and $R^2$ is an alkylene group having 1 to 4 carbon atoms, or

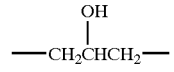

$X^{11}$ is a hydrogen atom or a methyl group,
$Y^{11}$ is a hydrogen atom or a methyl group, and
m is from 5 to 100.

4. The copolymer for cosmetics according to claim 1, wherein the mercapto-modified silicone is represented by the general formula:

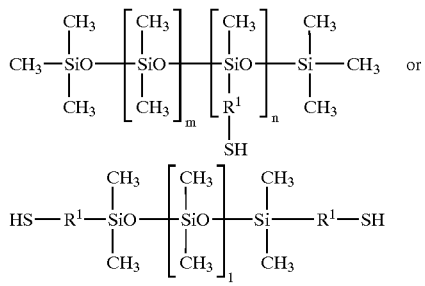

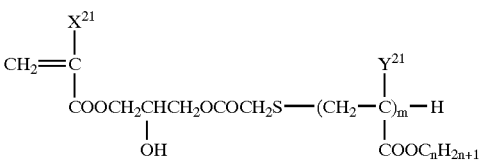

wherein $X^{21}$ and $Y^{21}$ are independently a hydrogen atom or a methyl group, n is from 1 to 22, and m is from 5 to 100.

wherein $R^1$ is a divalent saturated hydrocarbon group having 1 to 10 carbon atoms having a linear or branched carbon chain which may be intervened by one or two ether linkages, 1 is from 10 to 20, m is from 10 to 200 and n is from 1 to 10.

5. The copolymer according to claim 1, wherein the azo group-containing silicone is represented by the formula:

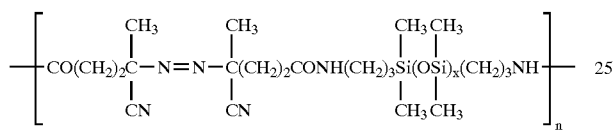

wherein x is from 10 to 200 and n is from 1 to 20.

6. The copolymer according to claim 1, wherein the polymerizable silane is represented by the formula:

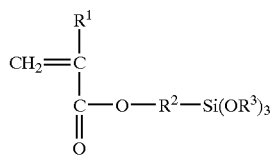

or

CH$_2$=CHSi (OR$^3$)$_3$ wherein $R^1$ is a methyl group or a hydrogen atom, $R^2$ is a divalent saturated hydrocarbon group having 1 to 10 carbon atoms having a linear or branched carbon chain which may be intervened by one or two ether linkages, and $R^3$ is an alkyl group having 1 to 4 carbon atoms.

7. The copolymer according to claim 2, wherein the polyalkyleneglycol (meth)acrylate is represented by formula (III-1):

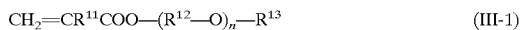

wherein $R^{11}$ and $R^{13}$ are a hydrogen atom or a methyl group, $R^{12}$ is an alkylene group having 2 to 6 carbon atoms, and n is an integer of from 1 to 50.

8. The copolymer according to claim 2, wherein the alkyl (meth)acrylate macromonomer is represented by formula (III-2):

9. The copolymer according to claim 1, wherein the alkyl (meth)acrylate is represented by formula (III-3):

wherein X is a hydrogen atom or a methyl group, and n is from 1 to 22.

10. A cosmetic composition comprising the copolymer according to any one of claims 1 to 9 dissolved or dispersed in a medium.

11. A cosmetic composition comprising 1 to 60% by weight of the copolymer according to any one of claims 1 to 9 dissolved or dispersed in a medium.

12. The cosmetic composition according to claim 11, wherein the medium is water or at least one organic solvent selected from the group consisting of a hydrocarbon-based solvent, an ester-based solvent, a ketone-based solvent, an alcohol-based solvent, a silicone-based solvent and a fluorine-containing solvent.

13. The cosmetic composition according to claim 12, wherein the fluorine-containing solvent is a hydrofluoroether represented by the formula:

wherein n is a number of from 1 to 12, m is a number of from 0 to 25, / is a number of from 0 to 11, m+/=2n+1, x is a number of from 1 to 12, y is a number of from 0 to 25, z is a number of from 0 to 11 and y+z=2x+1, provided that m and y are not simultaneously zero and / and z are not simultaneously zero.

14. A cosmetic composition comprising 0.1 to 30% by weight of the copolymer according to claim 1 as an essential component and additionally containing at least 0.1% by weight of a fluorine compound-treated powder and/or a fluorine-containing oil.

15. A cosmetic composition comprising a fluorine compound powder and/or a fluorine-containing oil compatibilized or dispersed into a fluorine-free compound with the copolymer according to claim 1 as a compatibilizing agent or a dispersing agent.

16. A cosmetic composition comprising a fluorine compound powder surface-treated with the copolymer according to claim 1.

17. The cosmetic according to any one of claims 14 to 16, wherein the fluorine compound-treated powder is a powder treated with a fluorine-containing phosphate ester represented by the general formula:

wherein Rf represents a polyfluoroalkyl or perfluoropolyether group having 6 to 16 carbon atoms, A represents an alkylene group having 1 to 4 carbon atoms, or

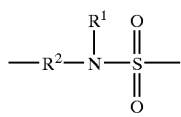

wherein $R^1$ is an alkyl group having 1 to 4 carbon atoms and $R^2$ is an alkylene group having 1 to 4 carbon atoms, or

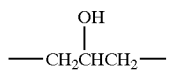

M represents a hydrogen atom, a metal atom, ammonium or substituted ammonium, and n represents a number of from 1 to 3.

18. The cosmetic according to claim 14 or 15, wherein the fluorine-containing oil is a perfluoropolyether, a hydrofluoroether or a compound represented by the general formula:

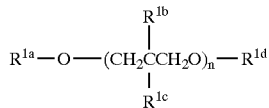

wherein $R^{1a}$ and $R^{1d}$ represent a hydrogen atom or a partly or completely fluorinated aliphatic group having 1 to 20 carbon atoms, $R^{1b}$ and $R^{1c}$ represent a hydrogen atom, an aliphatic group having 1 to 20 carbon atoms or a partly or completely fluorinated aliphatic group having 1 to 20 carbon atoms, provided that at least one of $R^{1a}$ to $R^{1d}$ is a partly or completely fluorinated aliphatic group having 1 to 20 carbon atoms, and n is a number of from 1 to 20, or by the general formula:

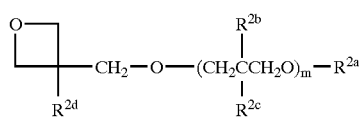

wherein $R^{2a}$ is a hydrogen atom or a partly or completely fluorinated aliphatic group having 1 to 20 carbon atoms, $R^{2b}$, $R^{2c}$ and $R^{2d}$ are an aliphatic group having 1 to 20 carbon atoms or a partly or completely fluorinated aliphatic group having 1 to 20 carbon atoms, provided that at least one of $R^{2a}$ to $R^{2d}$ is a partly or completely fluorinated aliphatic group having 1 to 20 carbon atoms, and m is a number of from 1 to 20.

19. A cosmetic composition comprising a silicone powder surface treated with the copolymer for cosmetics according to claim 1.

20. A cosmetic composition comprising a fluorine-containing oil in a fluorine-free solvent emulsified in a nonaqueous emulsion with a copolymer for cosmetics as an emulsifier, wherein the copolymer for cosmetics is the copolymer according to claim 1 or 2, the fluorine-free solvent is any one of a silicone-based solvent, a hydrocarbon-based solvent, an ester-based solvent and a ketone-based solvent, the fluorine-containing oil is a perfluoropolyether, a hydrofluoroether, or a compound represented by the formula:

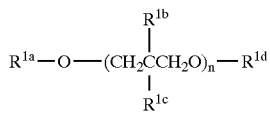

wherein $R^{1a}$ and $R^{1d}$ represent a hydrogen atom or a partly or completely fluorinated aliphatic group having 1 to 20 carbon atoms, $R^{1b}$ and $R^{1c}$ represent a hydrogen atom, an aliphatic group having 1 to 20 carbon atoms or a partly or completely fluorinated aliphatic group having 1 to 20 carbon atoms, provided that at least one of $R^{1a}$ to $R^{1d}$ is a partly or completely fluorinated aliphatic group having 1 to 20 carbon atoms, and n is a number of from 1 to 20, or by the formula:

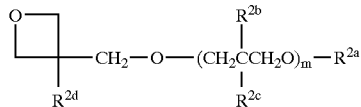

wherein $R^{2a}$ is a hydrogen atom or a partly or completely fluorinated aliphatic group having 1 to 20 carbon atoms, $R^{2b}$, $R^{2c}$ and $R^{2d}$ are an aliphatic group having 1 to 20 carbon atoms or a partly or completely fluorinated aliphatic group having 1 to 20 carbon atoms, provided that at least one of $R^{2a}$ to $R^{2d}$ is a partly or completely fluorinated aliphatic group having 1 to 20 carbon atoms, and m is a number of from 1 to 20.

\* \* \* \* \*